United States Patent
Badhwar et al.

(10) Patent No.: US 11,045,218 B2
(45) Date of Patent: Jun. 29, 2021

(54) TRANSATRIAL ACCESS FOR INTRACARDIAC THERAPY

(71) Applicant: University of Pittsburgh—Of the Commonwealth System of Higher Education, Pittsburgh, PA (US)

(72) Inventors: Vinay Badhwar, Sewickley, PA (US); Antonio D'Amore, Pittsburgh, PA (US); William R. Wagner, Gibsonia, PA (US)

(73) Assignees: University of Pittsburgh—of the Commonwealth System of Higher Education, Pittsburgh, PA (US); Ri.MED Foundation

(*) Notice: Subject to any disclaimer, the term of this patent is extended or adjusted under 35 U.S.C. 154(b) by 155 days.

(21) Appl. No.: 16/071,243

(22) PCT Filed: Jan. 20, 2017

(86) PCT No.: PCT/US2017/014341
§ 371 (c)(1),
(2) Date: Jul. 19, 2018

(87) PCT Pub. No.: WO2017/127682
PCT Pub. Date: Jul. 27, 2017

(65) Prior Publication Data
US 2019/0183524 A1 Jun. 20, 2019

Related U.S. Application Data

(60) Provisional application No. 62/281,422, filed on Jan. 21, 2016.

(51) Int. Cl.
*A61B 17/34* (2006.01)
*A61L 31/06* (2006.01)
(Continued)

(52) U.S. Cl.
CPC ...... *A61B 17/3423* (2013.01); *A61B 17/0469* (2013.01); *A61B 17/34* (2013.01);
(Continued)

(58) Field of Classification Search
CPC . A61B 17/0469; A61B 17/34; A61B 17/3423; A61B 2017/00004;
(Continued)

(56) References Cited

U.S. PATENT DOCUMENTS 6,033,426 A * 3/2000 Kaji .................. A61B 42/10
606/213
7,217,277 B2 5/2007 Parihar et al.
(Continued)

FOREIGN PATENT DOCUMENTS

| WO | 03077733 A2 | 9/2003 |
|----|---|---|
| WO | 2005030089 A2 | 4/2005 |
| WO | 2009127973 A2 | 10/2009 |

*Primary Examiner* — Erich G Herbermann
(74) *Attorney, Agent, or Firm* — The Webb Law Firm

(57) ABSTRACT

Disclosed herein are devices and methods for accessing the interior of the heart through a wall thereof. The device includes a main body, a flange at an end thereof, and a passage therethrough to allow for access to the interior of the heart when the device is placed on an outer surface thereof. The device can be formed of any suitable biocompatible and/or biodegradable material, and can have a passage sized to allow for transmittance of tools/devices normally used for interventions in the interior of the heart therethrough.

23 Claims, 9 Drawing Sheets

(51) Int. Cl.
  *A61B 17/04* (2006.01)
  *A61F 2/24* (2006.01)
  *A61B 17/00* (2006.01)

(52) U.S. Cl.
  CPC ............ *A61F 2/2427* (2013.01); *A61L 31/06* (2013.01); *A61B 2017/00004* (2013.01); *A61B 2017/00247* (2013.01); *A61B 2017/00292* (2013.01); *A61B 2017/00858* (2013.01); *A61B 2017/00862* (2013.01); *A61B 2017/00951* (2013.01); *A61B 2017/3425* (2013.01); *A61B 2217/007* (2013.01)

(58) Field of Classification Search
  CPC  A61B 2017/00247; A61B 2017/00292; A61B 2017/00858; A61B 2017/00862; A61B 2017/00951; A61B 2017/3425; A61B 2217/007; A61F 2/2427; A61L 31/06
  See application file for complete search history.

(56) References Cited

U.S. PATENT DOCUMENTS

| | | | |
|---|---|---|---|
| 2002/0138044 A1* | 9/2002 | Streeter | A61B 17/3421 604/198 |
| 2004/0024414 A1* | 2/2004 | Downing | A61F 2/2466 606/108 |
| 2008/0009859 A1 | 1/2008 | Auth et al. | |
| 2008/0161826 A1 | 7/2008 | Guiraudon | |
| 2008/0249504 A1* | 10/2008 | Lattouf | A61B 17/0218 604/511 |
| 2010/0280326 A1* | 11/2010 | Hess | A61B 17/3423 600/206 |
| 2011/0040324 A1* | 2/2011 | McCarthy | A61B 17/0218 606/215 |

* cited by examiner

TRANSATRIAL ACCESS FOR INTRACARDIAC THERAPY

CROSS-REFERENCE TO RELATED APPLICATIONS

This application is the United States national phase of International Application No. PCT/US2017/014341 filed Jan. 20, 2017, and claims to the benefit of U.S. Provisional Patent Application No. 62/281,422, filed Jan. 21, 2016, each of which is incorporated herein by reference in its entirety.

BACKGROUND

Field of the Invention

Described herein are devices for aiding repair and replacement of heart valves, and methods of using the same. More particularly, the devices and methods provide for transatrial access to the interior of the heart to allow for repair/replacement of both the mitral and tricuspid valves, along with device delivery to the atrial appendage and septal defect to facilitate therapy in adults and children.

Description of Related Art

In the field of heart valve repair and replacement, there are two primary means for accessing the interior of the heart to perform repair and replacement of tissue: by open-heart surgery and by transcatheter aortic valve replacement. Each presently-used technique has drawbacks.

Open-heart surgery, typically accomplished through use of a sternotomy, or "cracking" the sternum to access the heart, and a cardiopulmonary bypass (heart-lung) machine for directing blood away from the heart, is invasive. In addition, this technique is accompanied by a moderate to high risk of infection, blood loss, and blood clotting.

Transcatheter procedures involve accessing the interior of the heart by inserting a catheter into a blood vessel, for example the femoral artery (transfemoral), and then guiding the catheter to the region of interest within the heart. Transcatheter procedures for repair/replacement of the aortic or bicuspid valves can also be performed by accessing the aorta directly (transaortic), or by puncturing the wall of the heart directly (transapical), and can include transseptal access. For repair/replacement of the tricuspid valve, transjugular approaches are currently being attempted.

While less invasive than open-heart surgery, transcatheter procedures such as transfemoral, transaortic, and transjugular valve repair/replacement are more technically demanding due to space/sizing restrictions. Control of tools remotely, and in such a confined access path, increases demands on surgeons/cardiologists. Transapical procedures suffer from risks as well, such as loss of blood and infection, and due to the sensitive nature of the apex of the heart, are not preferred. Furthermore, these techniques are typically limited to repair/replacement of the aortic valve or the bicuspid (mitral) valve, though, as discussed above, repair/replacement of the tricuspid valve has been attempted through a transjugular approach.

Improvements in valve repair and replacement techniques, transapical or otherwise, and devices/equipment for the same, continue to be needed.

Access to the left atrial appendage requires transfemoral venous access and puncture of the inter-atrial septum to deliver devices. The similar approach is needed to access the inter-atrial septum and ventricular septum for catheter based repair. For larger bore devices or when femoral access is difficult, few options exist to directly access the cardiac chambers.

Accessing the atrial and ventricular chambers for the purposes of catheter based treatment of arrhythmias or electrical disturbances, requires similar femoral access that is associated with inherent limitations of size of devices to provide direct energy to the tissues.

SUMMARY OF THE INVENTION

Provided herein is a device useful in facilitating a safer and technically simpler surgically-assisted direct route for valve repair/replacement surgery or septal defect repair or atrial appendage therapy or arrhythmia therapy within all chambers of the heart. The medical device described herein can be used with an intercostal approach, providing a direct atrial access port. This intercostal approach, combined with the device disclosed herein, results in the ability to use a larger diameter cannula device, such as a catheter or trocar, which provides easier access to the atrium and permits easier manipulation of the heart valve in situ. Also provided are related methods of accessing the heart.

Provided herein is a medical device for transatrial heart access including a main body having a proximal end, a distal end having a tissue-engaging surface, and a sidewall therebetween defining a passage through the main body extending from the proximal end to the distal end, a flange disposed about the distal end of the main body and having a tissue-engaging surface, a proximal seal and a distal seal, the seals comprising a self-healing, elastomeric material, and a port in the sidewall in fluid communication with the passage.

In aspects the main body of the device has a frustoconical shape.

In aspects the tissue-engaging surface of the main body portion is contiguous with the tissue-engaging surface of the flange, which may be sutured to any cardiac structure.

In aspects the self-healing, elastomeric material of the seals is silicone.

In aspects the seals include a perforation, and the perforation forms a hemostatic seal when a surgical instrument is passed therethrough.

In aspects the main body and/or flange is formed of a biocompatible material, for example, polytetrafluoroethylene.

In aspects the main body and/or flange is formed of a biodegradable material, preferably poly(ether urethane) urea), poly(ether ester urethane) urea, or poly (ester carbonate urethane) urea.

In aspects, the flange comprises an adhesive on the tissue-engaging surface thereof. In further aspects, the adhesive is a biological polymer.

In aspects the flange includes one or more protuberances on the tissue-engaging surface thereof. In further aspects, the one or more protuberances are a barb or a ridge, such as concentric and/or annular ridges.

In aspects the passage of the device has a diameter of less than about 1 cm.

In aspects the passage of the device is configured to allow for passage of a medical device or tool having a size of from 3 F to 24 F therethrough.

Also provided herein is a kit including a device for transatrial heart access as described herein and at least one suture and/or a replacement heart valve and/or one or more tools for accessing the interior of a heart, preferably a catheter, access sheath, and/or trocar.

Also provided herein is a method of improving access to the interior of the heart of a patient, the method including a step of providing a device including a main body having a proximal end, a distal end having a tissue-engaging surface, and a sidewall therebetween defining a passage through the main body extending from the proximal end to the distal end, a flange disposed about the distal end of the main body and having a tissue-engaging surface, a proximal seal and a distal seal, the seals comprising a self-healing, elastomeric material, and a port in the sidewall in fluid communication with the passage. The method further includes a step of attaching the device to an outer surface of the heart.

In aspects the method further includes a step of removing the device from the outer surface of the heart.

In aspects of the method, the device is attached to the outer surface of the left atrium or the right atrium, preferably at the outer wall of the heart at or near the confluence of the right superior pulmonary vein (RSPV) and the interatrial groove.

In aspects of the method the main body of the device has a frustoconical shape.

In aspects of the method the tissue-engaging surface of the main body portion of the device is contiguous with the tissue-engaging surface of the flange.

In aspects of the method the self-healing, elastomeric material is silicone.

In aspects of the method the seals of the device include a perforation, and the perforation forms a hemostatic seal when a surgical instrument is passed therethrough.

In aspects of the method the main body of the device is formed of a biocompatible material, preferably polytetrafluoroethylene.

In aspects of the method the main body of the device is formed of a biodegradable material, preferably poly(ether urethane urea), poly(ether ester urethane) urea, or poly (ester carbonate urethane) urea.

In aspects of the method the flange of the device comprises an adhesive on the tissue-engaging surface thereof. In further aspects, the adhesive is a biological polymer.

In aspects of the method the flange comprises one or more protuberances on the tissue-engaging surface thereof. In further aspects, the one or more protuberances is a barb or a ridge, such as concentric and/or annular ridges.

In aspects of the method the flange of the device comprises one or more perforations.

In aspects of the method the step of attaching the device includes attaching the device to heart tissue by passing one or more sutures through the one or more perforations on the flange of the device. In further aspects the sutures are biodegradable.

In aspects of the method the passage of the device has a diameter of less than about 1 cm.

In aspects the method further includes a step of bleeding air from the passage through the port.

In aspects of the method the passage of the device is configured to allow for passage of a medical device or tool having a size of from 3 F to 24 F therethrough.

DETAILED DESCRIPTION OF THE INVENTION

Figure 1:
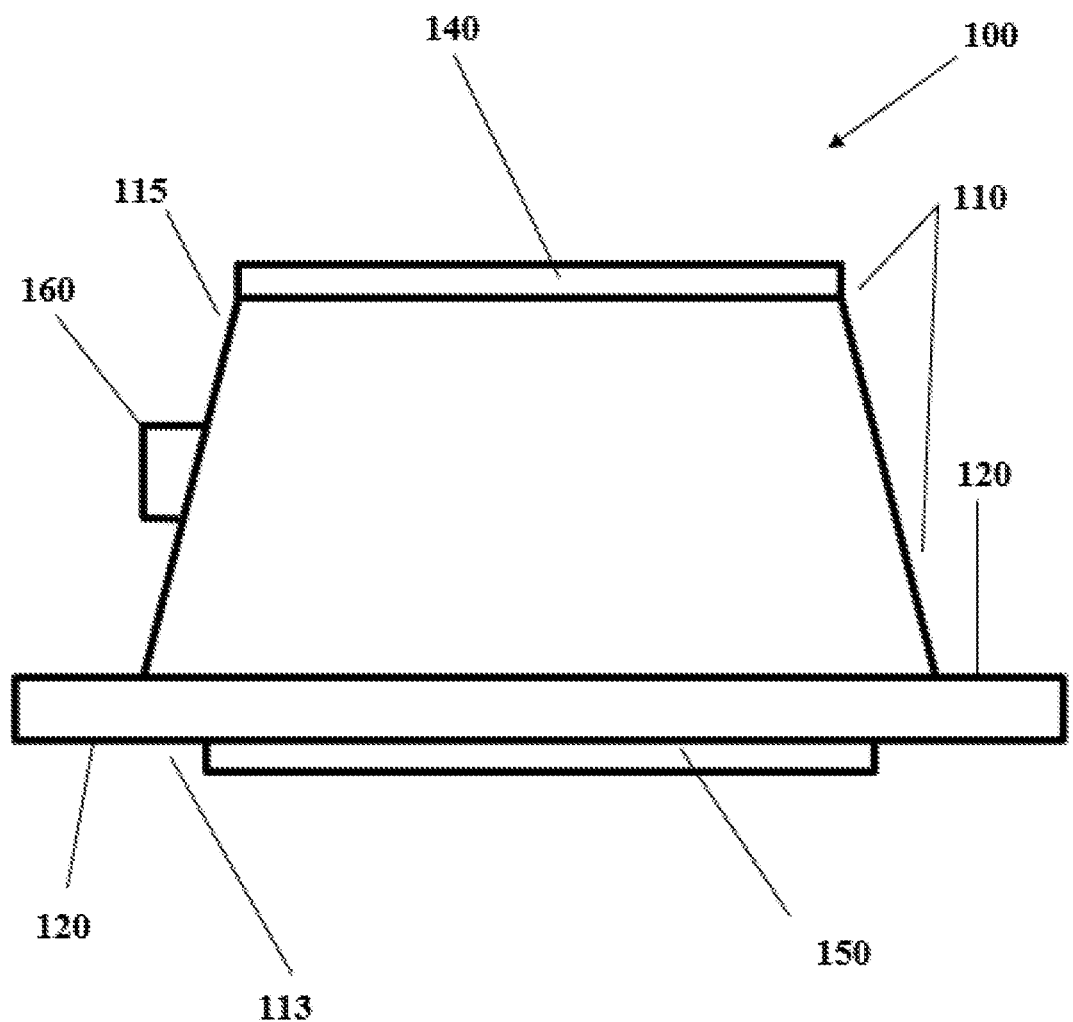
FIG. 1 shows a side view of a device according to one aspect of the present invention.

The following description is merely exemplary in nature and is in no way intended to limit the invention, its application, or uses. While the description is designed to permit one of ordinary skill in the art to make and use the invention, and specific examples are provided to that end, they should in no way be considered limiting. It will be apparent to one of ordinary skill in the art that various modifications to the following will fall within the scope of the appended claims. The present invention should not be considered limited to the presently disclosed aspects, whether provided in the examples or elsewhere herein.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more.

The figures accompanying this application are representative in nature, and should not be construed as implying any particular scale or directionality, unless otherwise indicated.

Provided herein are devices and methods of using the same that allow for secure, sealed access to the interior of the heart for repair and/or replacement of valves therein. Unlike currently available devices and methods, the present invention allows for repair/replacement of both the mitral (bicuspid) valve at the border of the left ventricle/atrium and the tricuspid valve at the border of the right ventricle/atrium.

The device of the present invention allows for intervention into, for example and without limitation, atrial walls to effect repair and/or replacement of either the mitral (bicuspid) valve (at the left atrial/ventricular interface) or the tricuspid valve (at the right atrial/ventricular interface). The device of the present invention also allows for access to the interior of the heart to address septal defects (both atrial and ventricular), and ablation of atrial or ventricular arrhythmias. Access can also include access to other cardiac structures, such as the atrial appendage (left atrial appendage). Moreover, while cardiac applications are exemplified in the present disclosure, the device, and methods of using the same, can be used to access any body cavity, for example, and without limitation, the esophagus, the stomach, the small intestine, the large intestine, and the lungs. These cavities can be accessed with the device described herein for, for example and without limitation, enteroscopy. Such access can include laparoscopic access to the bowel, affixing the device described herein to the organ, and passage of an enteroscope into the cavity to inspect for tumors in order to facilitate precise laparoscopic or robotic resection.

With reference to cardiac uses, the device improves options for cardiac intervention, as prior techniques (transfemoral, transaortic, transapical) allowed only for repair/replacement of aortic and mitral valves, and transjugular access for tricuspid valve repair/replacement is heretofore unvalidated and is fraught with the same shortcomings as other transcatheter approaches. Moreover, accessing the interior of the heart through transfemoral, transaortic, or transjugular routes involves applying substantial torque to the surgical device used to access and perform interventions, which can be undesirable. Among other benefits, the present invention ameliorates the need for such substantial torquing of tools/devices.

FIG. 1 shows a side view of a device 100 according to one aspect of the present invention. The device can be any suitable shape for facilitating attachment to the wall of the heart. The device includes a main body portion 110 having a distal end 113, a proximal end 115, and a flange 120 extending outward from the distal end 113. The distal end 113 is configured to contact the wall of the heart to which the device is attached, and the flange 120 of device 100 allows for secure attachment of the device to the outer wall of the heart, and increases hemostatic security. The flange 120 can be a separate component from, or formed integrally with, main body portion 110. Although the flange 120 can be attached to tissue by passing sutures therethrough, flange 120 optionally includes one or more perforations or holes for passage of sutures or other means for attaching device 100 to the outer surface of a heart. The main body 100 defines a passage (130 in other figures but not shown here) between the distal end 113 and the proximal end 115 of the main body 110. When the device 100 is attached to the wall of a heart, surgical tools, such as a catheter, are guided through passage 130 to the wall of the heart, for example an atrial wall, and therethrough to access the interior of the heart. In some aspects, as shown in FIG. 1, the main body portion 110 is frustoconical (trapezoidal along a cross-section of the longitudinal axis, circular along a cross-section of the transverse axis) in shape. However, both main body 110 and flange 120 can be any shape, so long as the assembly is functional for allowing access to the interior of the heart while maintaining adequate hemostasis.

Device 100 can be of any suitable size for placement on the heart, so that passage 130 is appropriately sized for introduction of tools into the heart to allow for repair/replacement of heart valves. In aspects the device is less than 2 inches across at its distal end, including flange 120. In other aspects, the device 100 is less than 1.5 inches across at its distal end, including flange 120. In aspects the device is less than 1 inch in height, from distal end 113 to proximal end 115. In aspects, the passage 130 has a diameter of less than about 2 cm. In aspects, the passage 130 has a diameter of less than about 1.5 cm. In some aspects, the passage 130 has a diameter of less than 1 cm. In aspects, the passage 130 has a diameter sufficient to allow for maintenance of hemostasis during insertion of a device having a diameter of from about 1 mm to about 8 mm therethrough. In some aspects, the passage 130 has a diameter suitable for the passage therethrough of a catheter or other sheathed medical device ranging in size from 3 F (French gauge) to 24 F.

With further reference to FIG. 1, device 100 includes a plurality of seals 140, 150. Seals are any device or structure that provides a hemostatic seal, e.g., that prevents passage of substantial amounts of blood or fluid when the device 100 is in use. That is, seals 140, 150 provide a hemostatic seal when device 100 is on the outer surface of a heart, including when a surgical tool or device is passed through passage 130 to access the interior of the heart.

As shown in FIG. 1, seals 140 and 150 are located at the distal end and proximal end of the main body 110 (or at the ends of the passage 130). However, it should be understood that the seals 140, 150 can be any number, and located at any suitable location, whether at the ends of or within the passage 130, so long as they provide adequate sealing capacity to maintain adequate hemostasis and/or prevent fluid from the heart, once the wall is punctured, from flowing or leaking from the heart out of the passage 130 at the proximal end 115. In some aspects, the device 100 includes two seals 140, 150 configured as shown in FIG. 1. Seals 140, 150 can each include perforations that allow for greater ease of insertion of surgical tools/devices through seals and into the interior of the heart. In aspects the perforations are self-healing.

With continuing reference to FIG. 1, device 100 also includes a port 160 for removal of air or gas and/or displacement of air or gas in passage 130 with a liquid, for example saline. Port 160 can also be useful for irrigation of the site of intervention. Those of skill will understand that port 160 can be of any size, so long as the port can effectively be used for removal/displacement of air that is built up in passage 130, or for irrigation of the site of intervention. Port 160 can be separated from passage 130 by a seal, such as seals 140, 150 as described below. In one aspect, the port 160 includes, or is adapted to receive a member of a tubing connector pair, such as a luer fitting or adapter pair, such as a male or female leur fitting, and, for example, can be slip-fit, barbed, or threaded. Such fittings, and specifications therefor, are broadly known and available. In one aspect, a compatible fitting is molded integrally into the port 160, and optionally is re-sealable, e.g., the passage within the port 160 comprises an elastomeric, self-healing seal or port 165 (see, FIG. 2) to maintain hemostasis. The tubing connector, e.g., luer fitting or adapter, can be configured to accept a mating member for connecting to medical devices to deliver irrigation or withdraw air from the passage 130. For example, and without limitation, port 160 can be threaded (male or female) for connection to a luer, which can be attached to a device for removing air or irrigation. A luer can also be attached to port 160 through a slip (press or friction) fit, barb, or otherwise retained to port 160. In other aspects, tubing is inserted directly into the port 160. In certain aspects a luer lock can be provided on the tubing.

Main body portion 110 and flange 120 of the device 100 can be formed out of any suitable, biocompatible material such as those known to those of skill in the art, for example metals (and oxides and alloys thereof) such as stainless steel, cobalt alloys, titanium alloys, aluminum oxide, zirconia, calcium phosphates, artificial or biological polymers or copolymers, silicones, poly (ethylene), poly(vinyl chloride), polyurethanes, polylactides, collagen, extracellular matrix gelatin, elastin, silk, polysaccharides, thermoplastics, polycarbonates, silicone and silicone derivatives, nylon, polypropylene, acrylics and acrylic derivatives. In aspects, the main body portion 110 is formed of synthetic polymers, thermoplastic elastomers, silicone elastomers, styrene block copolymers, thermoplastic copolyesters, thermoplastic polyamides, thermoplastic polyolefins, thermoplastic polyurethanes, thermoplastic vulcanizates, polyvinyl chloride, fluoropolymers, polyurethane, polycarbonate, silicone, acrylic compounds, thermoplastic polyesters, polypropylene, low density polyethylenes, nylon, sulfone resins, high density polyethylenes, polytetrafluoroethylenes and derivatives thereof, other synthetic biocompatible polymers, natural polymers, cellulose polymers, collagen, starch blends, other natural polymers, hyaluronic acid, alginates, carrageenan, biocompatible metals, gold, silver, other precious metals, stainless steel, titanium, other biocompatible metals, biocompatible ceramics, porcelain, alumina, hydroxyapatite, zirconia, or any material known to be biocompatible. In aspects, the material used for the device 100 has a modulus of elasticity (Young's modulus) of from about 1 MPa to about 100 GPa, including all subranges therebetween. In some aspects, the Young's modulus of the material is from about 8 to about 20 MPa, including all subranges therebetween. The main body portion and flange can be formed of the same biocompatible material; however, those of skill in the art will also appreciate that the main body portion can be formed of a rigid material, and the flange can be formed of a more flexible material, so that hemostasis can be maintained through movement of the heart muscle. In some aspects, for example where the device is attached to the left or right atrium, more compliant materials are utilized than would typically be used for devices for accessing the ventricles. In aspects, the device 100, including at least the main body portion 110 and flange 120, is/are formed of polytetrafluoroethylene (PTFE).

The seals 140, 150, and, optionally, any seal separating port 160 from passage 130, can be formed out of any suitable, biocompatible material known to those of skill in the art, such as natural or artificial elastomeric materials capable of self-healing such that when a surgical tool/device is removed from passage 130 (or port 160), seals 140, 150 reform a seal that maintains adequate hemostasis. These materials can include natural and artificial rubbers, silicone and silicone derivatives (such as fluorosilicone), and urethanes. Those of skill in the art will understand that any biocompatible, elastomeric material that can accept passage of surgical tools/devices of varying diameters/gauges and maintain a hemostatic seal therearound will be suitable, so long as it provides sufficient hemostasis and allows for entry and transmittance through passage 130 of a surgical device. In aspects, the seals 140, 150 are formed of silicone and are attached to the main body portion 110 of the device by one or more sutures. In aspects the one or more sutures are formed of polyester or polypropylene. In other aspects, the seals 140, 150 are attached to the main body portion 110 by an adhesive. In some aspects, the adhesive is a silicone-based adhesive, such as Sil-Poxy® (Smooth-On, Inc., Macungie, Pa.).

In some aspects, the main body portion 110 is formed of a biocompatible, biodegradable material such that it need not be removed from the heart following valve repair/replacement. In such aspects, the seals 140, 150 are similarly formed of a biocompatible, biodegradable material. By biocompatible and biodegradable it is meant that the material can be broken down by the natural processes of an organism into which the device 100 is introduced, and that neither the material that is utilized, nor components thereof that are released during breakdown of that material in the body, are harmful to living tissue within the organism or the organism itself.

The device 100 can be attached to the wall of the heart in any manner known to those of skill in the art. In aspects, the device 100 is attached by use of a suture, autosuture or a prolene/braided suture. Such sutures are available commercially from any number of medical suppliers, for example B. Braun Melsungen (Melsungen, Germany), Ethicon (Edinburgh, United Kingdom), and Covidien (Dublin, Republic of Ireland).

The device 100 can be attached to any area of the heart that allows for access to the interior thereof. In aspects, the device 100 is attached to the outer wall of the heart on the right atrium. In other aspects, the device 100 is attached to the outer wall of the heart at or near the confluence of the right superior pulmonary vein (RSPV) and Waterston's Groove (the interatrial groove).

Figure 2:
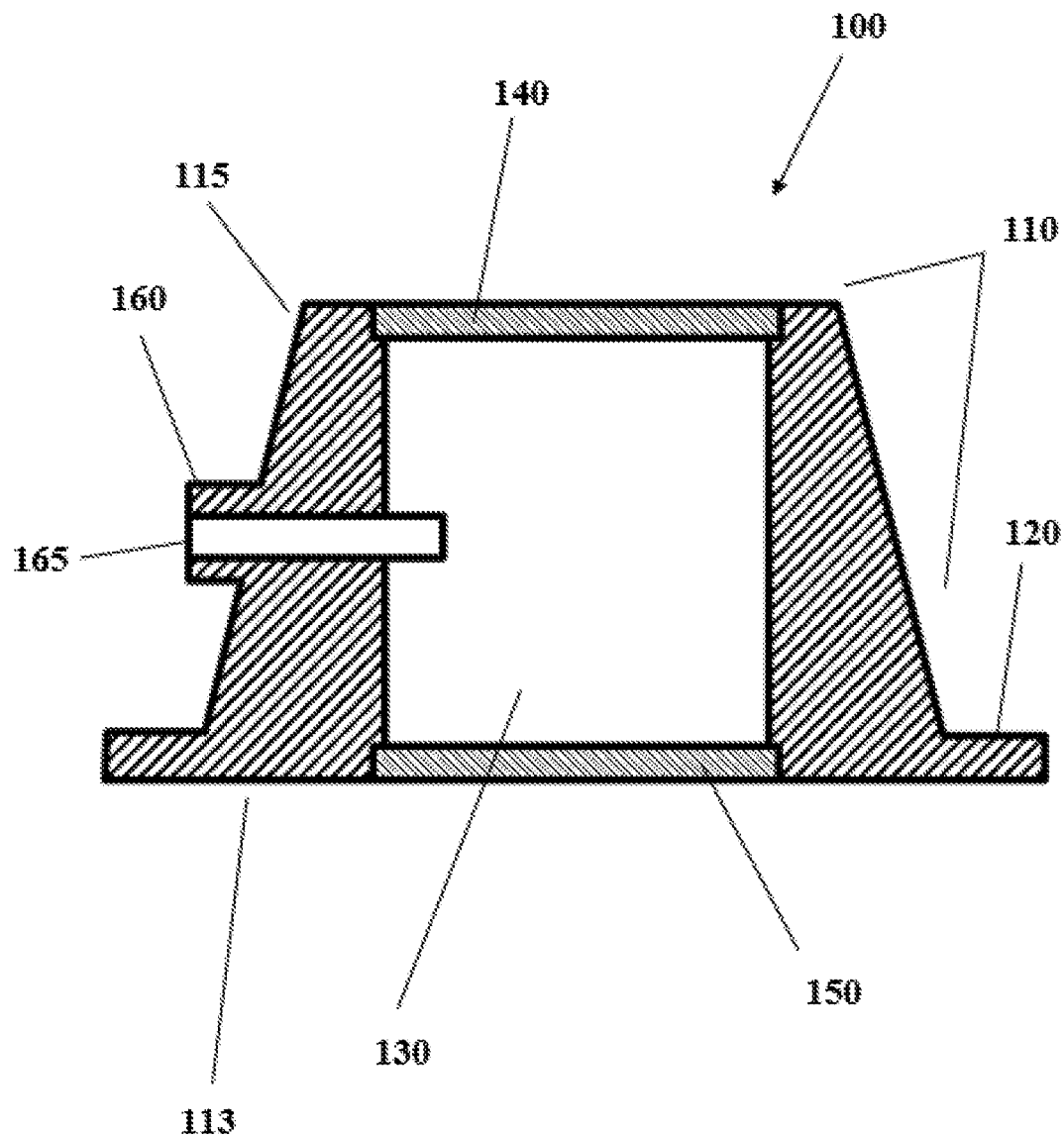
FIG. 2 shows a side cross-sectional view of a device according to one aspect of the present invention.

With reference to FIG. 2, shown is a cross-sectional view showing the interior of the device 100, including passage 130. Device 100 continues to include distal end 113, proximal end 115, flange 120, and proximal and distal seals 140, 150. Also shown is one arrangement of port 160, though those of skill in the art will appreciate that the port 160 can be of any configuration in relation to the outer surface of main body portion 110 and passage 130 so long as air/gas is effectively evacuated from the passage 130 without (or with minimal) concomitant fluid evacuation and/or liquid can be introduced into the passage 130.

Figure 3:
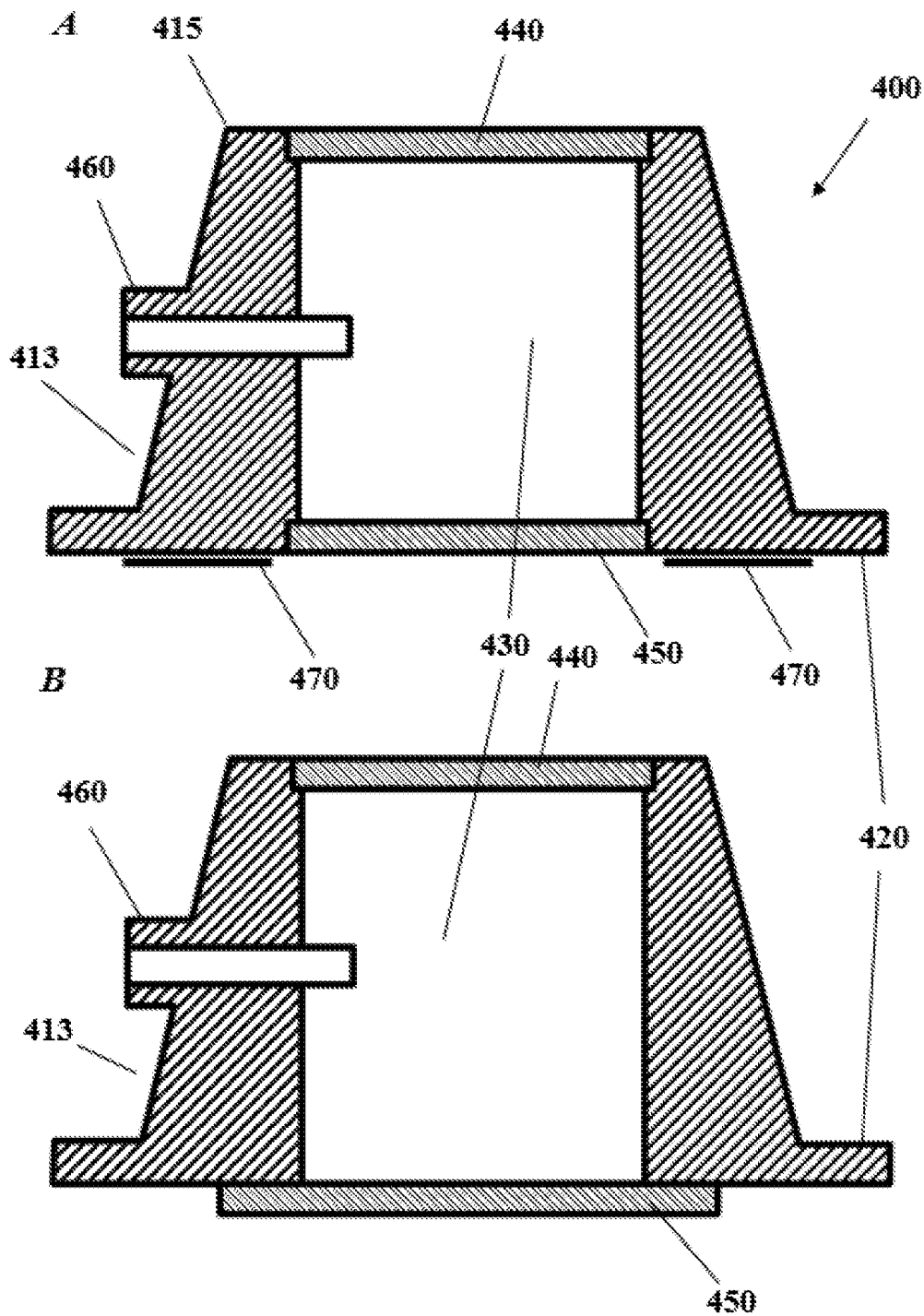
FIG. 3A-3B shows side cross-sectional views of a device according to one aspect of the present invention.

With reference to FIGS. 3A and 3B, shown is a cross-sectional view of a device 400 according to one aspect of the invention. As described previously, the device 400 includes a main body portion 410 having a distal end 413 and a proximal end 415, and a flange 420 extending outward from a distal end 413. The distal end 413 is configured to contact the wall of the heart to which the device is attached, and the flange 420 of device 400 allows for secure attachment of the device to the outer wall of the heart, and increases hemostatic security. The main body 400 defines a passage 430 between the distal end 413 and the proximal end 415 of the main body 410. When the device 400 is attached to the wall of a heart, surgical tools, such as a catheter, can be guided through passage 430 to the wall of the heart, and therethrough to access the interior of the heart. Device 400 also includes port 460 for release of air or gas that can build up in passage 430 and/or introduction of liquid into the passage 130.

With further reference to FIG. 3A, flange 420 in some aspects includes additional tissue-engagement means 470 for maintaining an adequate hemostatic seal with heart tissue. These means can be mechanical or chemical and can be included on any portion of flange 420 that would abut or come into contact with heart tissue when the device 400 is in use. Tissue-engagement means 470 can be any structural/mechanical element or chemical substance capable of increasing adhesion between the device 400 and tissue, to increase hemostatic security, and/or prevent device 400 from becoming dislodged from the tissue to which it is attached. In aspects the tissue-engagement means 470 can be protuberance(s), barbs or other elements that capture, grab, or increase the contact between flange 420 tissue, without causing undue damage to the underlying tissue and while also allowing for removal without undue trauma. While FIG. 3A shows a single protuberance, those of skill in the art will understand that any number of protuberances can be utilized, so that tissue trauma is minimized while adequate hemostasis is maintained. In FIG. 3A, a protuberance is provided as a perimetric (extending completely about the perimeter of distal seal 450 in any suitable closed shape, such as a polygon or closed curve such as a circle or an ellipse, or any closed shape comprising curves and/or line segments) annular ring or concentric rings on the distal end 413 and/or flange 420, on tissue-engaging portions thereof. In an aspect depicted in FIG. 3B, distal seal 450 serves as a protuberance.

In some aspects, the tissue-engagement means 470 is a chemical or biological adhesion-promoting substance, such as an adhesive. Suitable adhesives, whether based on natural or artificial products, include those formed from or based on artificial or biological polymers, acrylate and acrylate derivative adhesives, chitosan adhesives, fibrin glues and sealants, silicon adhesives, and the like are known to those of skill in the art. Preferably, an adhesive utilized as an attachment means is biocompatible, provides secure attachment of the device 400 for maintenance of hemostasis during movement of underlying heart tissue (i.e. a beating heart), and can be removed from the underlying tissue without causing undue trauma to such tissue. In aspects, attachment means is included on distal end 413 of device 400.

Figure 4:
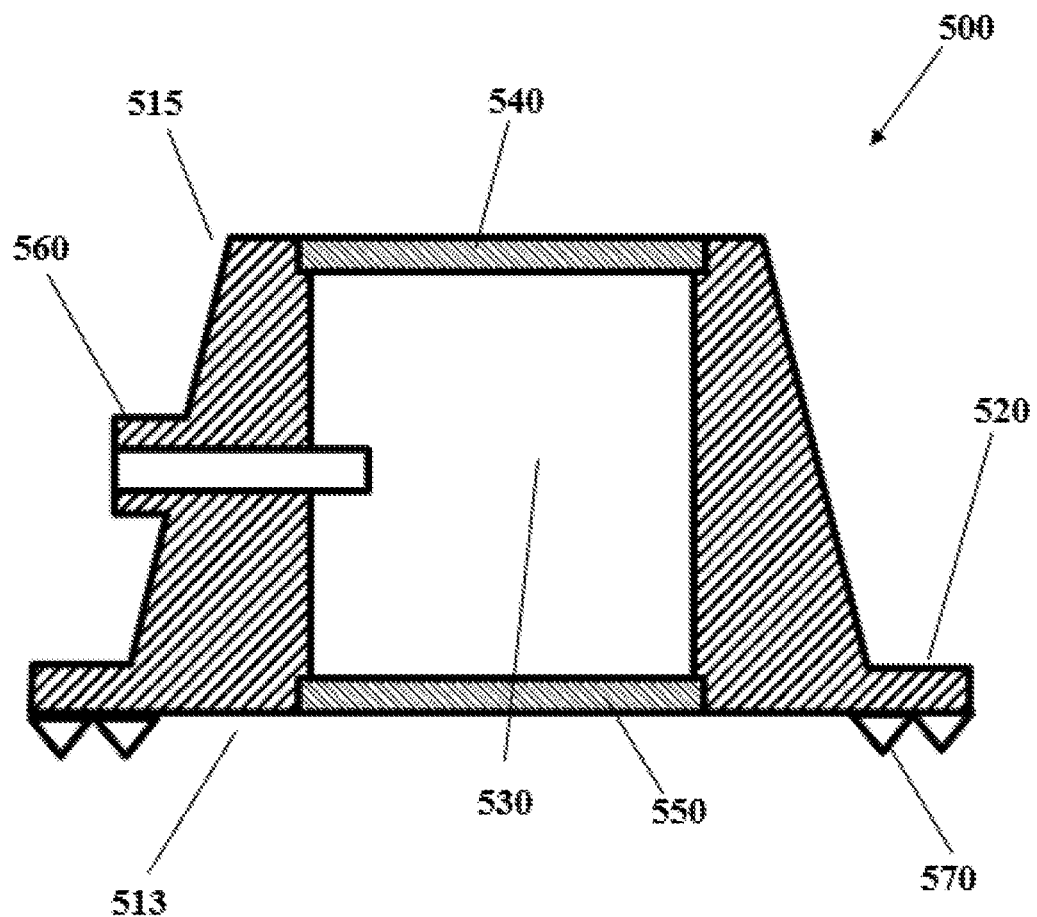
FIG. 4 shows a side cross-sectional view of a device according to one aspect of the present invention.

With reference to FIG. 4, shown is another aspect of a device 500 according to the present invention. Device 500 includes a main body portion 510 having a distal end 513 and a proximal end 515, and a flange 520 extending outward from a distal end 513. The distal end 513 is configured to contact the wall of the heart to which the device is attached, and the flange 520 of device 500 allows for secure attachment of the device to the outer wall of the heart, and increases hemostatic security. The main body 500 defines a passage 530 between the distal end 513 and the proximal end 515 of the main body 510. When the device 500 is attached to the wall of a heart, surgical tools, such as a catheter, can be guided through passage 530 to the wall of the heart, and therethrough to access the interior of the heart. Device 500 also includes port 560 for release of air or gas that can build up in passage 530 and/or delivery of liquid (irrigation) into the passage 530. Device 500 further includes a number of protuberances 570, e.g., concentric and/or annular ridges, displaced on a tissue-engaging surface of flange 520. As described previously, protuberances 570 can be included on flange 520, distal end 513 of device 500, or both.

Figure 5:
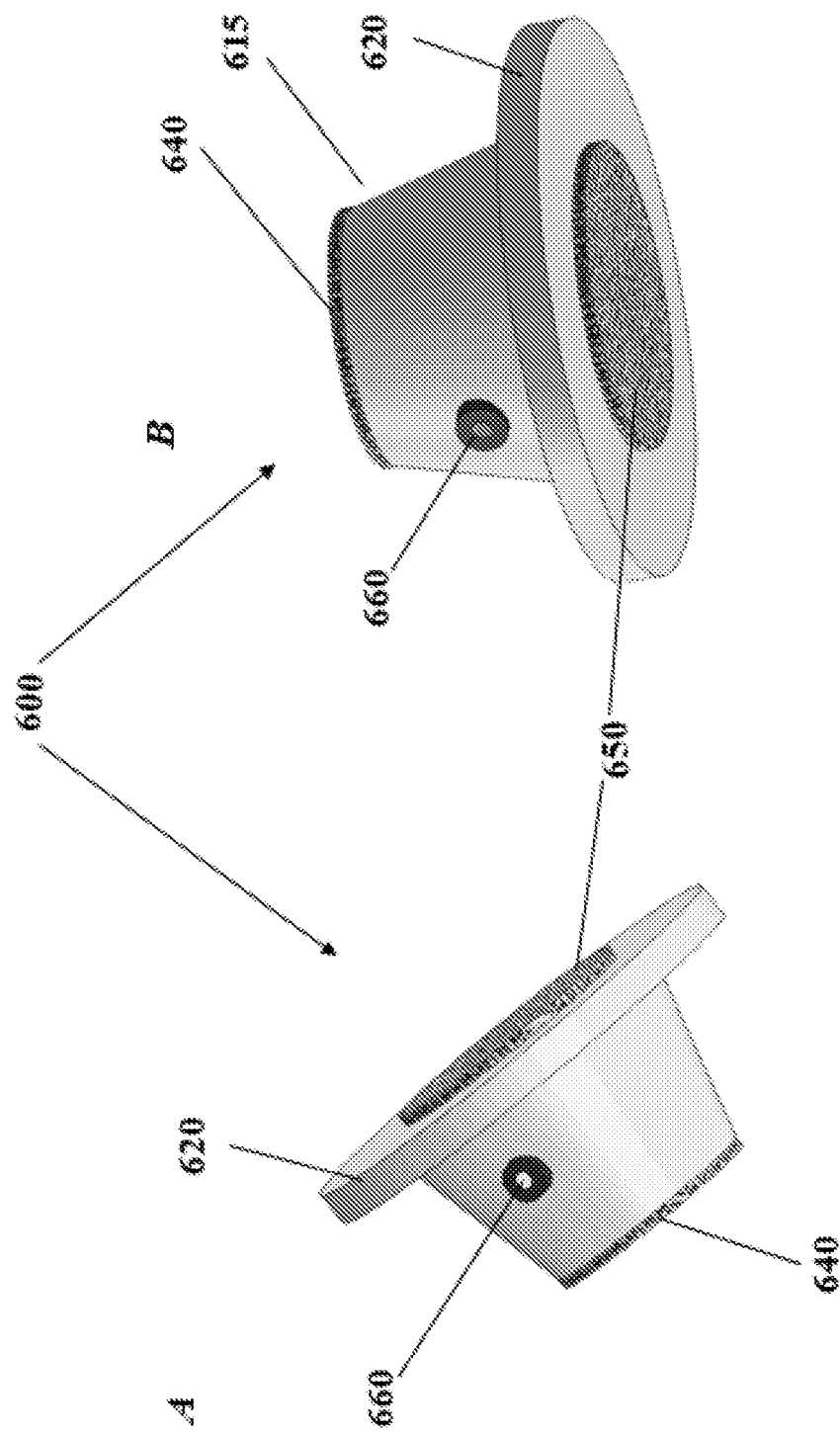
FIG. 5A-5B shows perspective views of a device according to one aspect of the present invention.

With reference to FIG. 5A-5B, shown are various three-dimensional perspective views of a device according to an aspect of the present invention. As described previously, the device 600 includes a main body portion 610 having a distal end 613 and a proximal end 615, and a flange 620 extending outward from a distal end 613. The distal end 613 is configured to contact the wall of the heart to which the device is attached, and the flange 620 of device 600 allows for secure attachment of the device to the outer wall of the heart, and increases hemostatic security. The main body 600 defines a passage (not shown) between the distal end 613 and the proximal end 615 of the main body 610. When the device 600 is attached to the wall of a heart, surgical tools, such as a catheter, can be guided through passage to the wall of the heart, and therethrough to access the interior of the heart. Device 600 also includes port 660 for release of air or gas that can build up in passage. As also described above, while device 600 has a frustoconical shape in FIG. 6A-6B, those of skill in the art will understand that the shape of device 600 can be adapted, so long as it maintains adequate hemostasis during interventions that involve access to the interior of the heart, including seals 640, 650 for maintaining hemostasis while allowing a surgical tool/device to pass through passage.

Figure 6:
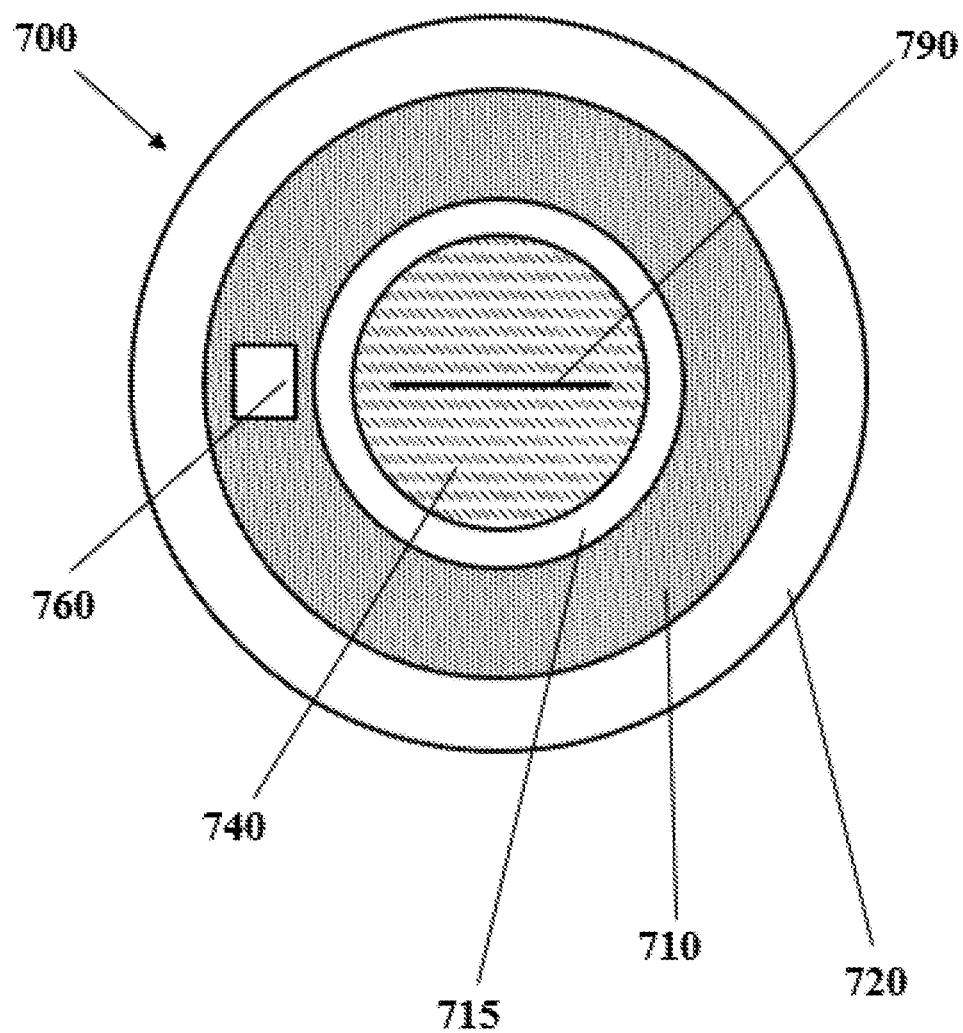
FIG. 6 shows a top view of a device according to one aspect of the present invention.

With reference to FIG. 6, shown is a top view of a device 700 according to an aspect of the present invention. Shown is main body portion 710, including proximal end 715, flange 720, and seal 740. Seal 740 includes elastically-deformable perforation 790 that allows for a surgical tool/device to pass through seal 740, while also allowing the seal 740 to maintain contact with the outer portion of the tool/device to maintain hemostasis. Device 700 also includes port 760 for release of air or gas that can build up in passage (not shown) and/or delivery of liquid (irrigation) into the passage. As described above, while device 700 is shown having a particular shape, the shape of device 700 can be changed.

Figure 7:
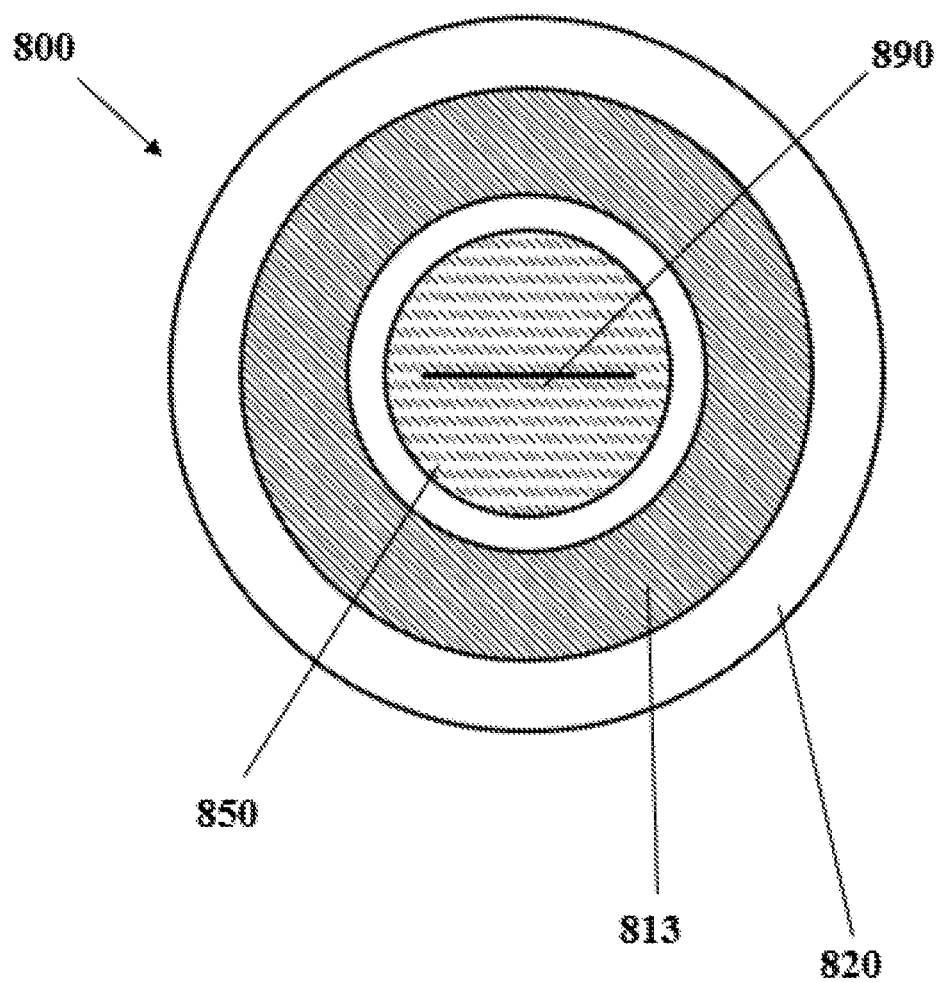
FIG. 7 shows a bottom view of a device according to one aspect of the present invention.

With reference to FIG. 7, shown is a bottom view of a device 800 according to an aspect of the present invention. Shown is distal end 815, flange 820, and seal 850. Seal 850 includes perforation 890 that allows for a surgical tool/device to pass through seal 850, while also allowing the seal 850 to maintain contact with the outer portion of the tool/device to maintain hemostasis. As described above, while device 800 is shown having a particular shape, the shape of device 800 can be changed.

While the device and methods of the present invention can be accomplished by any suitable means, in certain aspects, the device is delivered by accessing the heart through a minimally invasive non rib-spreading thoracic incision. As used herein, the term "minimally invasive incision" means any incision in the chest or abdomen of a patient (human or otherwise) that allows for access to the pleural or peritoneal cavity and that allows access to internal organs including, at least, the heart. A minimally invasive incision can occur by any means known to those of ordinary skill in the art, for example and without limitation antero-laterally (through the anterior chest wall, typically a 3 cm incision below the breast or pectoral area through the $4^{th}$ or $5^{th}$ intercostal space at the level of the anterior axillary line) or across the costal margin posterolaterally (incision through an intercostal space on the patient's back, typically in the submammary fold below the scapula). A subset of minimally invasive incisions for access to thoracic organs my include thoracotomy as well as sternotomy. As used herein, "sternotomy" means a minimally invasive technique in which an incision allows for the sternum to be accessed and partially divided, to allow for access to the pleural cavity. A sternotomy useful for the present methods can be partial or full, though a partial is less invasive and is preferred in some aspects.

In some preferred aspects, the device of the present invention is delivered through a minithoracotomy. In aspects, the minithoracotomy is a right minithoracotomy. In some aspects, the technique involves an incision in the fourth intercostal space, within centimeters of the AA (anterior axillary) line. As used herein, "AA line" means an imaginary vertical line on the body wall continuing the line of the anterior axillary fold with the upper arm. As used herein, "axillary fold" mean the ridges of skin-covered muscle along the sides of the chest where the underside of the arm meets the shoulder. The anterior fold is formed by the pectoralis major muscle (lateral edge). In some aspects the incision is within 1 to 10, 2 to 9, 2 to 8, 2 to 7, 2 to 6, 2 to 5, 2 to 4, or 2 to 3 cm of the AA line.

In some aspects, methods of using the device of the present invention include replacement of a heart valve. In aspects, the valve to be replaced is a mitral valve or a tricuspid valve. In other aspects, methods of using the device of the present invention include inserting a new valve within an existing valve that is diseased or otherwise malfunctioning. Suitable replacement valves include those known to those of skill in the art, including those produced by Edwards LifeSciences (Irvine, Calif.), St. Jude Medical (St. Paul, Minn.), LivaNova (London, United Kingdom), Medtronic (Dublin, Republic of Ireland), Abbott Vascular (Abbot Park, Ill. USA), Boston Scientific (Marlborough, Mass., USA). Another suitable valve replacement is that as described in International Patent Publication No. WO 2016/138423, the content of which is incorporated herein in reference in their entirety.

In aspects, methods of using the device described herein include accessing the heart through any known means as described above, for example and without limitation through a right minithoracotomy. The device is attached to the outer wall of the heart at a location suitable for accessing the region of the heart where valve repair/replacement, or other intervention requiring access to the interior of the heart, is to take place. In aspects, to access the left side cardiac structures, the device is attached to the outer wall of the heart at or near the confluence of the right superior pulmonary vein (RSPV) and Waterston's Groove (the interatrial groove). In aspects, to access the right side cardiac structures or atrial septum, the device is attached to the outer wall of the heart at the right atrium. In aspects, the device is attached through use of sutures. In some aspects, the device includes an additional attachment means. In aspects, the attachment means (mechanical or biological/chemical) is provided on some or all of a tissue-engaging surface of flange and/or distal end of the device. The presence of seals allows for surgical interventions on the interior of the heart to be performed by passing a tool/device through the seals and passage, while maintaining hemostasis, and attachment means can, in certain aspects, allow for maintenance of hemostasis. Upon completion of the intervention, the device, including any suturing of the wall of the heart, may be removed. In other aspects, the device, including seals, is formed of a biocompatible, biodegradable material and the device is not removed following the intervention. In aspects where the device includes tubing and a luer fitting attached to or part of port 160, and where the device remains in place following the intervention, the tubing and luer can be removable.

Once the device is in place on the heart, the interior of the heart is accessed using tools known to those of skill in the heart. Accordingly, as described previously, passage is sized to accommodate known devices/tools and to maintained adequate hemostasis during passage of such tools therethrough (and through seals). Tools and devices utilized for such procedures, and for which passage and seals are sized include, without limitation, trocars, catheters, and introducer sheaths produced by Edwards LifeSciences (Irvine, Calif.), Medtronic (Dublin, Republic of Ireland), Covidien (Dublin, Republic of Ireland), Micro Interventional Devices, Inc. (Newton, Pa.), Vivitro Labs, Inc. (Victoria, Canda), Apica Cardiovascular (Galaway, Republic of Ireland), Cordis (Hialeah, Fla.), and Boston Scientific (Marlborough, Mass.).

Figure 8:
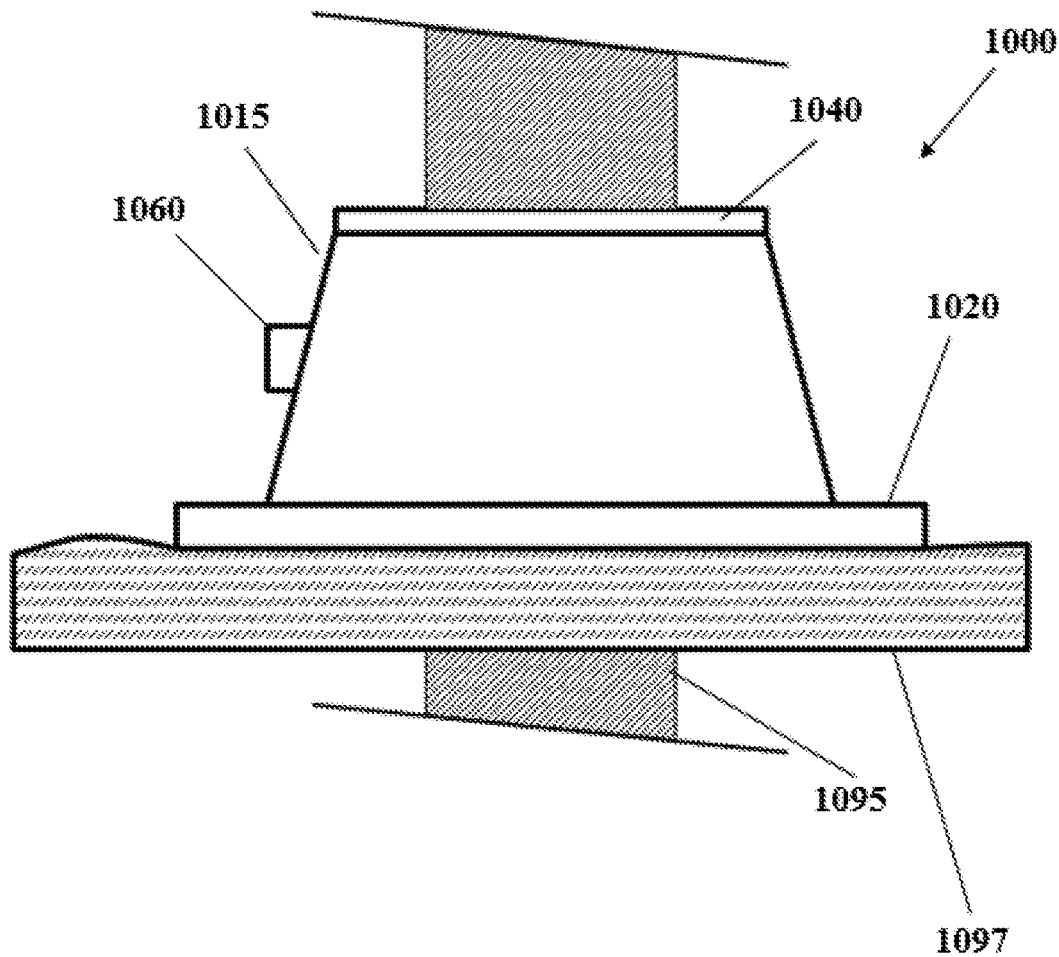
FIG. 8 shows a side view of a device according to one aspect of the present invention in use.

With reference to FIG. 8, shown is an elevation view of a device 1000 as described herein in use, with a portion of a surgical tool/device 1095 passing through the seals and the passage (not shown). As described previously, device 1000 includes a main body portion 1010 having a distal end and a proximal end 1015, and a flange 1020 extending outward from a distal end. The distal end is configured to contact the wall of the heart 1097 to which the device is attached, and the flange 1020 of device 1000 allows for secure attachment of the device to the outer wall of the heart, and increases hemostatic security. The main body 1010 defines a passage (not shown) between the distal end 1013 and the proximal end 1015 of the main body 1010. When the device 1000 is attached to the wall of a heart, surgical tools, such as a catheter, can be guided through passage to the wall of the heart, and therethrough to access the interior of the heart. Device 1000 also includes port 1060 for release of air or gas that can build up in passage. As also described above, while device 1000 has a frustoconical shape in FIG. 10, those of skill in the art will understand that the shape of device 1000 can be adapted, so long as it maintains adequate hemostasis during interventions that involve access to the interior of the heart, including seal 1040 (distal seal not shown) for maintaining hemostasis while allowing a surgical tool/device to pass through passage.

Figure 9:
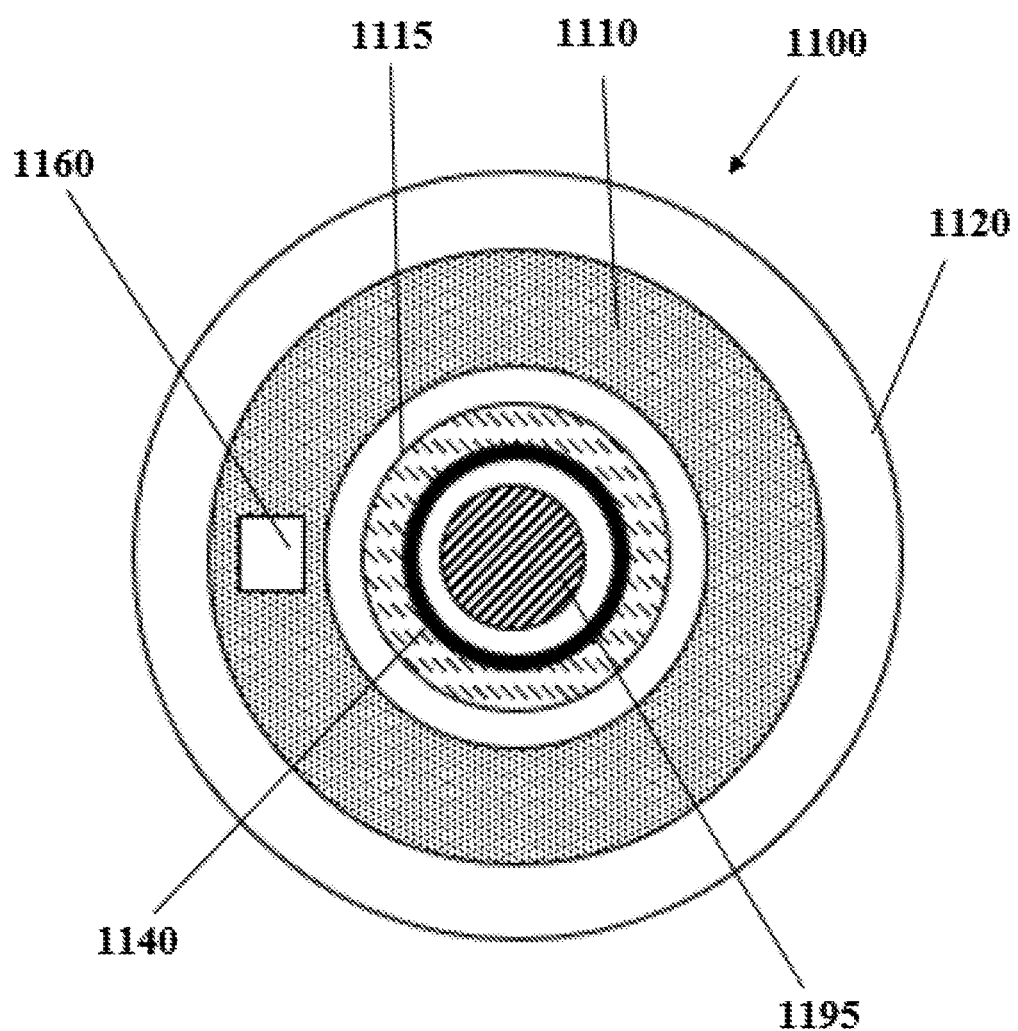
FIG. 9 shows a top view of a device according to one aspect of the present invention in use.

With reference to FIG. 9, shown is a top view of a device 1100 as described herein in use, with a surgical tool/device 1195, shown in cross-section, passing through the passage (not shown). As described previously, device 1000 includes a main body portion 1110 having a distal end and a proximal end 1115, a port 1160, and a flange 1120 extending outward from a distal end. The distal end is configured to contact the wall of the heart to which the device is attached, and the flange 1120 of device 1100 allows for secure attachment of the device to the outer wall of the heart, and increases hemostatic security.

For ease, a device according to the present invention as described herein can be included in a kit with other components useful for performing heart valve repair/replacement. That is, a kit can include a device as described herein and a replacement valve (such as, for example, any of those described above), or a device as described herein and a trocar, access catheter, and/or access sheath (such as, for example, any of those described above), or a device as described herein, a replacement valve, and a trocar, access catheter, and/or access sheath.

CLAUSES

1. A medical device for transatrial heart access comprising:
   a main body having a proximal end, a distal end having a tissue-engaging surface, and a sidewall therebetween defining a passage through the main body extending from the proximal end to the distal end;
   a flange disposed about the distal end of the main body and having a tissue-engaging surface;
   a proximal seal and a distal seal, the seals comprising a self-healing, elastomeric material; and
   a port in the sidewall in fluid communication with the passage.
2. The medical device of clause 1, wherein the main body has a frustoconical shape.
3. The medical device of clause 1 or clause 2, wherein the tissue-engaging surface of the main body portion is contiguous with the tissue-engaging surface of the flange.
4. The medical device of any of clauses 1-3, wherein the self-healing, elastomeric material is silicone.
5. The medical device of any of clauses 1-4, wherein the seals each include a perforation, and wherein the perforations form a hemostatic seal when a surgical instrument is passed therethrough.
6. The medical device of any of clauses 1-5, wherein the main body and/or flange is formed of a biocompatible material, preferably polytetrafluoroethylene.
7. The medical device of any of clauses 1-5, wherein the main body and/or flange is formed of a biodegradable material, preferably poly(ether urethane urea), poly(ether ester urethane) urea, or poly (ester carbonate urethane) urea.
8. The medical device of any of clauses 1-7, wherein the flange comprises an adhesive on the tissue-engaging surface thereof.
9. The medical device of clause 8, wherein the adhesive is a biological polymer.
10. The medical device of any of clauses 1-9, wherein the flange comprises one or more protuberances on the tissue-engaging surface thereof.

11. The medical device of clause 10, wherein the one or more protuberances are one or more barbs or ridges, such as concentric and/or annular ridges.
12. The medical device of any of clauses 1-11, wherein the passage has a diameter of less than about 1 cm.
13. The medical device of any of clauses 1-12, wherein the passage of the device is configured to allow for passage of a medical device or tool having a size of from 3 F to 24 F therethrough.
14. A kit comprising a device according to any of clauses 1-13 and at least one suture and/or a replacement heart valve and/or one or more tools for accessing the interior of a heart, preferably a catheter, access sheath, and/or trocar.
15. A method of improving access to the interior of the heart of a patient, comprising:
   providing a device comprising
   a main body having a proximal end, a distal end having a tissue-engaging surface, and a sidewall therebetween defining a passage through the main body extending from the proximal end to the distal end;
   a flange disposed about the distal end of the main body and having a tissue-engaging surface;
   a proximal seal and a distal seal, the seals comprising a self-healing, elastomeric material; and
   a port in the sidewall in fluid communication with the passage; and
   attaching the device to an outer surface of the heart.
16. The method of clause 15, wherein the method further comprises a step of removing the device from the outer surface of the heart.
17. The method of clause 15 or clause 16, wherein the device is attached to the outer surface of the left atrium or the right atrium, preferably at the outer wall of the heart at or near the confluence of the right superior pulmonary vein (RSPV) and the interatrial groove.
18. The method of any of clauses 15-17, wherein the main body of the device has a frustoconical shape.
19. The method of any of clauses 15-18, wherein the tissue-engaging surface of the main body portion of the device is contiguous with the tissue-engaging surface of the flange.
20. The method of any of clauses 15-19, wherein the self-healing, elastomeric material is silicone.
21. The method of any of clauses 15-20, wherein the seals of the device each include a perforation, and wherein the perforations form a hemostatic seal when a surgical instrument is passed therethrough.
22. The method of any of clauses 15-21, wherein the main body of the device is formed of a biocompatible material, preferably polytetrafluoroethylene.
23. The method of any of clauses 15-21, wherein the main body of the device is formed of a biodegradable material, preferably poly(ether urethane urea), poly(ether ester urethane) urea, or poly (ester carbonate urethane) urea.
24. The method of any of clauses 15-23, wherein the flange of the device comprises an adhesive on the tissue-engaging surface thereof.
25. The method of clause 24, wherein the adhesive is a biological polymer.
26. The method of any of clauses 15-25, wherein the flange comprises one or more protuberances on the tissue-engaging surface thereof.
27. The method of clause 26, wherein the one or more protuberances are one or more barbs or ridges, such as concentric and/or annular ridges.
28. The method of any of clauses 15-27, wherein the flange of the device comprises one or more perforations.
29. The method of clause 28, wherein the step of attaching the device comprises attaching the device to heart tissue by passing one or more sutures through the one or more perforations on the flange of the device.
30. The method of clause 29, wherein the sutures are biodegradable.
31. The method of any of clauses 15-30, wherein the passage of the device has a diameter of less than about 1 cm.
32. The method of any of clauses 15-31, further comprising bleeding air from the passage through the port.
33. The method of any of clauses 15-32, wherein the passage of the device is configured to allow for passage of a medical device or tool having a size of from 3 F to 24 F therethrough.
34. A method of improving access to the interior of a body cavity, comprising:
   providing a device comprising
   a main body having a proximal end, a distal end having a tissue-engaging surface, and a sidewall therebetween defining a passage through the main body extending from the proximal end to the distal end;
   a flange disposed about the distal end of the main body and having a tissue-engaging surface;
   a proximal seal and a distal seal, the seals comprising a self-healing, elastomeric material; and
   a port in the sidewall in fluid communication with the passage; and
   attaching the device to an outer surface of a body cavity.
35. The method of clause 35, wherein the body cavity is selected from the group consisting of the esophagus, stomach, small intestine, large intestine, and lungs.

While the present invention has been described in terms of the above examples and detailed description, those of ordinary skill will understand that alterations may be made within the spirit of the invention. Accordingly, the above should not be considered limiting, and the scope of the invention is defined by the appended claims.

What is claimed is:

1. A medical device for transatrial heart access comprising: a main body having a proximal end, a distal end, and a sidewall therebetween defining a passage through the main body extending from the proximal end to the distal end, wherein the passage is configured to allow for passage of a medical device or tool having a size of 3 F to 24 F therethrough; a flange disposed about the distal end of the main body comprising an annular proximal surface, an annular distal surface, and a peripheral edge extending therebetween, wherein the distal surface comprises a tissue-engaging surface configured, upon the complete deployment of the medical device for transatrial heart access, to directly contact an outer surface of a heart; a proximal seal and a distal seal connected to the main body, the seals comprising a self-healing, elastomeric material, wherein the distal seal comprises a distal surface configured, upon the complete deployment of the medical device, to directly contact the outer surface of the heart, the distal surface being (i) contiguous with the tissue-engaging surface of the flange or (ii) positioned distal to the tissue-engaging surface flange; and a port in the sidewall in fluid communication with the passage.

2. The medical device of claim 1, wherein the main body has a frustoconical shape, and where an external diameter of the proximal end of the main body is less than an external diameter of the distal end of the main body.

3. The medical device of claim 1, wherein the self-healing, elastomeric material is silicone, and wherein the passage has a diameter of less than about 1 cm.

4. The medical device of claim 1, wherein the seals each include a perforation, and wherein the perforations form a hemostatic seal when a surgical instrument is passed therethrough.

5. The medical device of claim 1, wherein the main body or the flange is formed of one or more of polytetrafluoroethylene, poly(ether urethane urea), poly(ether ester urethane) urea, or poly (ester carbonate urethane) urea.

6. The medical device of claim 5, wherein the flange comprises an adhesive on the tissue-engaging surface thereof.

7. The medical device of claim 5, wherein the flange comprises one or more protuberances on the tissue-engaging surface thereof, the one or more protuberances comprising one or more barbs or concentric and/or annular ridges.

8. A kit comprising a device according to claim 1 and at least one suture, a replacement heart valve, or one or more tools for accessing the interior of a heart.

9. The medical device of claim 1, wherein the proximal seal comprises a proximal surface that is (i) contiguous with the proximal end of the main body or (ii) positioned proximal to the proximal end of the main body.

10. The medical device of claim 1, wherein the distal seal is partially positioned in the passage and in contact with the sidewall defining the passage, and wherein the distal surface of the distal seal is distal to the tissue-engaging surface of the flange.

11. The medical device of claim 1, wherein the distal seal extends distally as a protuberance from the tissue-engaging surfaces of the flange.

12. The medical device of claim 1, wherein the flange comprises an annular protuberance on the tissue-engaging surface thereof extending completely about a perimeter of the distal seal.

13. A method of improving access to an interior of a heart of a patient, comprising: providing a device comprising: a main body having a proximal end, a distal end, and a sidewall therebetween defining a passage through the main body extending from the proximal end to the distal end, wherein the passage is configured to allow for passage of a medical device or tool having a size of 3 F to 24 F therethrough; a flange disposed about the distal end of the main body comprising an annular proximal surface, an annular distal surface, and a peripheral edge extending therebetween, wherein the distal surface comprises a tissue-engaging surface configured to directly contact an outer surface of a heart; a proximal seal and a distal seal connected to the main body, the seals comprising a self-healing, elastomeric material, wherein the distal seal comprises a distal surface that is (i) contiguous with the tissue-engaging surface of the flange or (ii) is positioned distal to the tissue-engaging surface of the flange; a port in the sidewall in fluid communication with the passage; and attaching the device to the outer surface of the heart, such that the tissue engaging surface of the flange and the distal surface of the distal seal directly contact the outer surface of the heart.

14. The method of claim 13, wherein the method further comprises after attaching the device to the outer surface of the heart, removing the device from the outer surface of the heart.

15. The method of claim 13, wherein attaching the device to the outer surface of the heart comprises attaching the device to an outer surface of the left atrium or the right atrium.

16. The method of claim 13, wherein the main body of the device has a frustoconical shape, and where an external diameter of the proximal end of the main body is less than an external diameter of the distal end of the main body.

17. The method of claim 13, wherein the tissue-engaging surface of the main body of the device is contiguous with the tissue-engaging surface of the flange.

18. The method of claim 13, wherein the self-healing, elastomeric material is silicone, and wherein the seals of the device each include a perforation, and wherein the perforations form a hemostatic seal when a surgical instrument is passed therethrough.

19. The method of claim 13, wherein the main body of the device is formed of one or more of polytetrafluoroethylene, poly(ether urethane urea), poly(ether ester urethane) urea, or poly (ester carbonate urethane) urea.

20. The method of claim 13, wherein the flange of the device comprises an adhesive on the tissue-engaging surface thereof.

21. The method of claim 13, wherein the flange comprises one or more protuberances on the tissue-engaging surface thereof, the one or more protuberances comprising one or more barbs or concentric and/or annular ridges.

22. The method of claim 13, wherein the flange of the device comprises one or more perforations, and wherein attaching the device to the outer surface of the heart comprises attaching the device to heart tissue by passing one or more sutures through the one or more perforations on the flange of the device.

23. The method of claim 13, further comprising bleeding air from the passage through the port.

* * * * *

UNITED STATES PATENT AND TRADEMARK OFFICE
CERTIFICATE OF CORRECTION

PATENT NO.        : 11,045,218 B2
APPLICATION NO.   : 16/071243
DATED             : June 29, 2021
INVENTOR(S)       : Vinay Badhwar et al.

Page 1 of 1

It is certified that error appears in the above-identified patent and that said Letters Patent is hereby corrected as shown below:

On the Title Page

Column 1, Assignees, Line 4, after "Foundation" insert -- , (IT) --

In the Claims

Column 14, Line 58, Claim 1, after "surface" insert -- of the --

Column 16, Lines 6-7, Claim 13, delete "tissue engaging" and insert -- tissue-engaging --

Signed and Sealed this
Eleventh Day of January, 2022

Drew Hirshfeld
*Performing the Functions and Duties of the*
*Under Secretary of Commerce for Intellectual Property and*
*Director of the United States Patent and Trademark Office*